United States Patent
D'Alessio

(10) Patent No.: US 10,952,709 B2
(45) Date of Patent: Mar. 23, 2021

(54) EXTENDED TIP SPRAY APPLICATOR FOR TWO-COMPONENT SURGICAL SEALANT, AND METHODS OF USE THEREOF

(71) Applicant: HyperBranch Medical Technology, Inc., Durham, NC (US)

(72) Inventor: Keith R. D'Alessio, Carey, NC (US)

(73) Assignee: HyperBranch Medical Technology, Inc., Durham, NC (US)

( * ) Notice: Subject to any disclaimer, the term of this patent is extended or adjusted under 35 U.S.C. 154(b) by 24 days.

(21) Appl. No.: 14/677,382

(22) Filed: Apr. 2, 2015

(65) Prior Publication Data

US 2015/0282794 A1 Oct. 8, 2015

Related U.S. Application Data

(60) Provisional application No. 61/975,328, filed on Apr. 4, 2014.

(51) Int. Cl.
A61B 17/00 (2006.01)

(52) U.S. Cl.
CPC .............. *A61B 17/00491* (2013.01); *A61B 2017/00495* (2013.01); *A61B 2017/00522* (2013.01); *A61B 2017/00544* (2013.01); *A61B 2017/00853* (2013.01); *A61B 2017/00862* (2013.01)

(58) Field of Classification Search
CPC .... A61B 17/00491; A61B 2017/00495; A61B 2017/00522; A61B 2017/00526; A61B 2017/00535; A61B 2017/00539; A61B 2017/00534; A61B 2017/00853; A61B 2017/00862
See application file for complete search history.

(56) References Cited

U.S. PATENT DOCUMENTS

| | | |
|---|---|---|
| 3,092,964 A | 6/1963 | Martin et al. |
| 3,112,074 A | 11/1963 | Green |
| 3,214,102 A | 10/1965 | Meyer |
| 3,495,544 A | 2/1970 | Enssle |
| 3,828,980 A | 8/1974 | Creighton et al. |
| 4,040,420 A | 8/1977 | Speer |
| 4,071,196 A | 1/1978 | Burke et al. |

(Continued)

FOREIGN PATENT DOCUMENTS

| CA | 2150253 A1 | 4/1995 |
|---|---|---|
| DE | 29516077 U1 | 2/1997 |

(Continued)

OTHER PUBLICATIONS

International Preliminary Report on Patentability for PCT/US2015/023974 dated Oct. 13, 2016.

(Continued)

*Primary Examiner* — Robert A Lynch
(74) *Attorney, Agent, or Firm* — Lerner, David, Littenberg, Krumholz & Mentlik, LLP

(57) ABSTRACT

Provided is an extended length, flexible or bendable spray tip assembly for use with a multi-component surgical sealant. The tip assembly is particularly suited for use in surgical procedures having limited access to a surgical field, for example, neurosurgical procedures involving infratentorial, skull base, or transsphenoidal craniotomy, as well as the spine. The tip assembly can be used in combination with a multi-component delivery system or applicator.

23 Claims, 5 Drawing Sheets

(56) References Cited

U.S. PATENT DOCUMENTS

| | | |
|---|---|---|
| 4,359,049 A | 11/1982 | Redl et al. |
| 4,538,920 A | 9/1985 | Drake |
| 4,631,055 A | 12/1986 | Redl et al. |
| 4,706,888 A | 11/1987 | Dobbs |
| 4,735,616 A | 4/1988 | Eibl et al. |
| 4,753,536 A | 6/1988 | Spehar et al. |
| 4,767,026 A | 8/1988 | Keller et al. |
| 4,767,416 A | 8/1988 | Wolf et al. |
| 4,826,048 A | 5/1989 | Skorka et al. |
| 4,842,581 A | 6/1989 | Davis |
| 4,846,405 A | 7/1989 | Zimmermann |
| 4,874,368 A | 10/1989 | Miller et al. |
| 4,902,281 A | 2/1990 | Avoy |
| 4,978,336 A | 12/1990 | Capozzi et al. |
| 4,979,942 A | 12/1990 | Wolf et al. |
| 5,033,650 A | 7/1991 | Colin et al. |
| 5,049,135 A | 9/1991 | Davis |
| 5,080,649 A | 1/1992 | Vetter |
| 5,104,375 A | 4/1992 | Wolf et al. |
| 5,116,315 A | 5/1992 | Capozzi et al. |
| 5,249,709 A | 10/1993 | Duckworth et al. |
| 5,249,862 A | 10/1993 | Herold et al. |
| 5,290,228 A | 3/1994 | Uemura et al. |
| 5,328,462 A | 7/1994 | Fischer |
| 5,333,760 A | 8/1994 | Simmen |
| 5,334,163 A | 8/1994 | Sinnett |
| 5,341,993 A | 8/1994 | Haber et al. |
| 5,360,410 A | 11/1994 | Blacks |
| 5,368,563 A | 11/1994 | Lonneman et al. |
| 5,413,253 A | 5/1995 | Simmen |
| 5,445,614 A | 8/1995 | Haber et al. |
| 5,474,540 A | 12/1995 | Miller et al. |
| 5,582,596 A | 12/1996 | Fukunaga et al. |
| 5,605,255 A | 2/1997 | Reidel et al. |
| 5,605,541 A | 2/1997 | Holm |
| 5,643,206 A | 7/1997 | Fischer |
| 5,645,855 A | 7/1997 | Lorenz |
| 5,656,035 A | 8/1997 | Avoy |
| 5,678,764 A | 10/1997 | Kukesh |
| 5,740,965 A | 4/1998 | Miyagi et al. |
| 5,759,171 A | 6/1998 | Coelho et al. |
| 5,810,885 A | 9/1998 | Zinger |
| 5,819,988 A | 10/1998 | Sawhney et al. |
| 5,876,384 A * | 3/1999 | Dragan ............... A61M 1/008 433/91 |
| 5,887,755 A | 3/1999 | Hood, III |
| 5,890,655 A | 4/1999 | Collias et al. |
| 5,941,462 A | 8/1999 | Sandor |
| 5,980,866 A | 11/1999 | Uchida et al. |
| 6,004,547 A | 12/1999 | Rowe et al. |
| 6,047,861 A | 4/2000 | Vidal et al. |
| 6,059,749 A | 5/2000 | Marx |
| 6,065,645 A | 5/2000 | Sawhney et al. |
| 6,113,571 A | 9/2000 | Zinger et al. |
| 6,132,396 A | 10/2000 | Antanavich et al. |
| 6,143,805 A | 11/2000 | Hickey et al. |
| 6,161,730 A | 12/2000 | Heusser et al. |
| 6,206,905 B1 | 3/2001 | Holm et al. |
| 6,228,051 B1 | 5/2001 | Trumbull |
| 6,234,356 B1 | 5/2001 | Garbasch et al. |
| 6,248,800 B1 | 6/2001 | Greff et al. |
| 6,251,370 B1 | 6/2001 | Uchida et al. |
| 6,310,166 B1 | 10/2001 | Hickey et al. |
| 6,322,852 B1 | 11/2001 | Leung |
| 6,328,229 B1 | 12/2001 | Duronio et al. |
| 6,379,373 B1 | 4/2002 | Sawhney et al. |
| 6,398,761 B1 | 6/2002 | Bills et al. |
| 6,422,865 B1 * | 7/2002 | Fischer ............... A61C 5/40 433/81 |
| 6,454,786 B1 | 9/2002 | Holm et al. |
| 6,461,325 B1 | 10/2002 | Delmotte et al. |
| 6,461,361 B1 | 10/2002 | Epstein |
| 6,468,520 B1 | 10/2002 | Rowe et al. |
| 6,527,749 B1 | 3/2003 | Roby et al. |
| 6,540,716 B1 | 4/2003 | Holm |
| 6,565,539 B1 | 5/2003 | Zinger et al. |
| 6,579,916 B1 | 6/2003 | Askill et al. |
| 6,585,696 B2 | 7/2003 | Petersen et al. |
| 6,609,666 B1 | 8/2003 | Blake |
| 6,613,020 B1 | 9/2003 | Holm et al. |
| 6,648,852 B2 | 11/2003 | Wirt et al. |
| 6,673,093 B1 | 1/2004 | Sawhney |
| 6,698,622 B2 | 3/2004 | Sawhney et al. |
| 6,752,292 B2 | 6/2004 | Van Herpen |
| 6,769,574 B1 | 8/2004 | Keller |
| 6,773,414 B2 | 8/2004 | Ljungquist |
| 6,783,514 B2 | 8/2004 | Tovey et al. |
| 6,820,766 B2 | 11/2004 | Keller et al. |
| 6,835,186 B1 | 12/2004 | Pennington et al. |
| 6,852,099 B2 | 2/2005 | Redl et al. |
| 6,874,657 B2 | 4/2005 | Metzner et al. |
| 6,884,232 B1 | 4/2005 | Hagmann et al. |
| 6,921,381 B2 | 7/2005 | Spero et al. |
| 6,949,114 B2 | 9/2005 | Milo et al. |
| 6,960,340 B2 | 11/2005 | Rowe et al. |
| 6,994,686 B2 | 2/2006 | Cruise et al. |
| 7,009,034 B2 | 3/2006 | Pathak et al. |
| 7,037,289 B2 | 5/2006 | Dodge et al. |
| 7,037,490 B2 | 5/2006 | Rowe et al. |
| 7,077,339 B2 | 7/2006 | Leach |
| 7,124,574 B2 | 10/2006 | Horn et al. |
| 7,124,914 B2 | 10/2006 | Foster et al. |
| 7,128,278 B2 | 10/2006 | Archambeau et al. |
| 7,131,597 B2 | 11/2006 | Scattergood |
| 7,140,558 B2 | 11/2006 | McCracken et al. |
| 7,140,560 B2 | 11/2006 | Stotts et al. |
| 7,140,797 B2 | 11/2006 | Hunter et al. |
| 7,152,396 B2 | 12/2006 | Cheng |
| 7,152,813 B2 | 12/2006 | Chen |
| 7,156,835 B2 | 1/2007 | Epstein |
| 7,159,796 B2 | 1/2007 | Yquel |
| 7,164,133 B2 | 1/2007 | Hjertman et al. |
| 7,172,733 B2 | 2/2007 | Gauthier et al. |
| 7,173,733 B2 | 2/2007 | Nino et al. |
| 7,178,742 B2 | 2/2007 | Mellentine et al. |
| 7,178,743 B2 | 2/2007 | Clarke, III et al. |
| 7,178,744 B2 | 2/2007 | Tapphorn et al. |
| 7,182,279 B2 | 2/2007 | Wang |
| 7,185,829 B2 | 3/2007 | Sundholm |
| 7,191,917 B2 | 3/2007 | Brinz et al. |
| 7,191,959 B2 | 3/2007 | Kutay et al. |
| 7,195,135 B1 | 3/2007 | Garcia et al. |
| 7,195,180 B2 | 3/2007 | Lee |
| 7,201,336 B2 | 4/2007 | Blette et al. |
| 7,207,969 B2 | 4/2007 | Epstein et al. |
| 7,217,254 B2 | 5/2007 | Kirwan et al. |
| 7,222,752 B2 | 5/2007 | Ponton |
| 7,223,426 B2 | 5/2007 | Cheng et al. |
| 7,225,999 B2 | 6/2007 | Foianini et al. |
| 7,232,080 B2 | 6/2007 | Kutay et al. |
| 7,232,082 B2 | 6/2007 | Muhlhausen et al. |
| 7,237,693 B2 | 7/2007 | Brennan et al. |
| 7,237,726 B2 | 7/2007 | Yu |
| 7,244,248 B2 | 7/2007 | Azzolini |
| 7,246,758 B2 | 7/2007 | Wang |
| 7,252,243 B2 | 8/2007 | Bjorn et al. |
| 7,252,247 B2 | 8/2007 | Holm et al. |
| 7,264,179 B2 | 9/2007 | Robbins |
| 7,267,288 B2 | 9/2007 | Wheeler, Jr. et al. |
| 7,270,654 B2 | 9/2007 | Griego et al. |
| 7,275,699 B2 | 10/2007 | Schmidt |
| 7,278,985 B2 | 10/2007 | Ågerup |
| 7,332,566 B2 | 2/2008 | Pathak et al. |
| 7,347,850 B2 | 3/2008 | Sawhney |
| 7,351,249 B2 | 4/2008 | Hnojewyj et al. |
| 7,427,607 B2 | 9/2008 | Suzuki |
| 7,537,174 B2 | 5/2009 | Redl et al. |
| 7,592,418 B2 | 9/2009 | Pathak et al. |
| 7,611,494 B2 | 11/2009 | Campbell et al. |
| 7,682,336 B2 | 3/2010 | Hoogenakker et al. |
| 7,731,678 B2 | 6/2010 | Tennican et al. |
| 7,811,291 B2 | 10/2010 | Liu et al. |
| 7,833,216 B2 | 11/2010 | Voegele et al. |
| 7,846,125 B2 | 12/2010 | Yatabe et al. |

(56) References Cited

U.S. PATENT DOCUMENTS

| | | |
|---|---|---|
| 7,896,849 B2 | 3/2011 | Delay |
| 8,003,705 B2 | 8/2011 | Sawhney et al. |
| 8,033,483 B2 | 10/2011 | Fortier et al. |
| 8,057,426 B2 | 11/2011 | Nayak et al. |
| 8,057,427 B2 | 11/2011 | Griffiths et al. |
| 8,066,678 B2 | 11/2011 | Vaillancourt et al. |
| 8,152,777 B2 | 4/2012 | Campbell et al. |
| 8,210,453 B2 | 7/2012 | Hull et al. |
| 8,262,608 B2 | 9/2012 | Clark et al. |
| 8,287,566 B2 | 10/2012 | Leopold et al. |
| 8,292,846 B2 | 10/2012 | Sargeant et al. |
| 8,303,531 B2 | 11/2012 | Sharratt |
| 8,323,262 B2 | 12/2012 | D'Alessio et al. |
| 8,343,183 B2 | 1/2013 | D'Alessio et al. |
| 8,357,147 B2 | 1/2013 | Burkinshaw et al. |
| 8,376,989 B2 | 2/2013 | Rissman et al. |
| 8,377,507 B2 | 2/2013 | Wawrzyniak et al. |
| 8,387,899 B2 | 3/2013 | Fortier et al. |
| 8,408,480 B2 | 4/2013 | Hull et al. |
| 8,469,289 B2 | 6/2013 | Redl et al. |
| 8,534,575 B2 | 9/2013 | Brem |
| 8,545,457 B2 | 10/2013 | Hayakawa |
| 8,616,468 B2 | 12/2013 | Hull et al. |
| 8,640,921 B2 | 2/2014 | Meron et al. |
| 8,641,662 B2 | 2/2014 | Barker, Jr. et al. |
| 8,672,237 B2 | 3/2014 | Roush et al. |
| 8,684,282 B2 | 4/2014 | Steffen |
| 8,827,980 B2 | 9/2014 | Ji |
| 8,876,021 B2 | 11/2014 | Fortier et al. |
| 8,973,596 B2 | 3/2015 | Hull |
| 8,974,436 B2 | 3/2015 | Sherman et al. |
| 9,101,946 B2 | 8/2015 | Hull et al. |
| 9,125,633 B2 | 9/2015 | Roush et al. |
| 9,179,898 B2 | 11/2015 | Redl et al. |
| 9,205,207 B2 | 12/2015 | Ji |
| 9,211,554 B2 | 12/2015 | Brunk et al. |
| 9,211,555 B2 | 12/2015 | Meron et al. |
| 9,370,630 B2 | 6/2016 | Greter |
| 9,381,005 B2 | 7/2016 | Masson et al. |
| 9,433,959 B2 | 9/2016 | Krauss et al. |
| 9,445,795 B2 | 9/2016 | Ohri et al. |
| 9,486,190 B2 | 11/2016 | Sherman et al. |
| 9,517,478 B2 | 12/2016 | Hull et al. |
| 9,572,555 B1 | 2/2017 | Lai et al. |
| 9,579,449 B2 | 2/2017 | Sharma et al. |
| 9,586,005 B2 | 3/2017 | Steffen |
| 9,622,731 B2 | 4/2017 | Peindl et al. |
| 9,629,966 B2 | 4/2017 | Ji |
| 9,681,860 B2 | 6/2017 | Steffen |
| 9,700,290 B2 | 7/2017 | Hull et al. |
| 9,782,549 B2 | 10/2017 | Riebman et al. |
| 2002/0022588 A1 | 2/2002 | Wilkie et al. |
| 2002/0176732 A1 | 11/2002 | Quintero et al. |
| 2004/0050963 A1* | 3/2004 | Ray ............... B05B 1/3046 239/321 |
| 2006/0045900 A1 | 3/2006 | Richard et al. |
| 2007/0083086 A1* | 4/2007 | LeVahn ............ A61B 17/02 600/210 |
| 2007/0196454 A1* | 8/2007 | Stockman ........ A61K 31/785 424/445 |
| 2007/0203451 A1* | 8/2007 | Murakami ......... A61M 5/282 604/82 |
| 2008/0195040 A1 | 8/2008 | Clark et al. |
| 2009/0124986 A1* | 5/2009 | Hayakawa ........ B01F 5/0262 604/290 |
| 2009/0199848 A1 | 8/2009 | Sharratt |
| 2010/0114158 A1 | 5/2010 | Hattan et al. |
| 2010/0280312 A1* | 11/2010 | D'Alessio ..... A61B 17/00491 600/104 |
| 2011/0015736 A1* | 1/2011 | Sharim ......... A61B 17/00234 623/11.11 |
| 2013/0110161 A1 | 5/2013 | Sherman et al. |
| 2013/0146679 A1 | 6/2013 | Fortier et al. |
| 2013/0338631 A1 | 12/2013 | Butlin et al. |
| 2014/0012184 A1 | 1/2014 | Lynch |
| 2014/0014213 A1 | 1/2014 | Hull |
| 2014/0088645 A1* | 3/2014 | Sengun ......... A61B 17/8875 606/232 |

FOREIGN PATENT DOCUMENTS

| | | |
|---|---|---|
| DE | 69127614 T2 | 4/1998 |
| DE | 69827132 T2 | 3/2006 |
| DE | 60108786 T2 | 4/2006 |
| EP | 0170526 A2 | 2/1986 |
| EP | 0689874 A1 | 1/1996 |
| EP | 0814866 A1 | 1/1998 |
| EP | 1188455 A1 | 3/2002 |
| EP | 1955660 A2 | 8/2008 |
| EP | 2111918 A2 | 10/2009 |
| EP | 2 311 376 A1 | 4/2011 |
| FR | 2869533 A1 | 11/2005 |
| GB | 1469009 A | 3/1977 |
| WO | 9629113 A1 | 9/1996 |
| WO | 9902207 A1 | 1/1999 |
| WO | 2002005898 A1 | 1/2002 |
| WO | WO-02/055138 A1 | 7/2002 |
| WO | 02076534 A1 | 10/2002 |
| WO | 03047530 A2 | 6/2003 |
| WO | 2005009225 A2 | 2/2005 |
| WO | 2005048984 A1 | 6/2005 |
| WO | 2005103184 A1 | 11/2005 |
| WO | 2006034128 A2 | 3/2006 |
| WO | 2006060055 A1 | 6/2006 |
| WO | 2007127903 A2 | 11/2007 |
| WO | 2007131371 A1 | 11/2007 |
| WO | WO-2009/097271 A1 | 8/2009 |
| WO | 2014008445 A1 | 1/2014 |

OTHER PUBLICATIONS

International Search Report and Written Opinion from corresponding PCT application PCT/US2015/023974 dated Jul. 26, 2015.

Extended European Search Report issued by the European Patent Office in corresponding Application No. 15772951.8, dated Nov. 6, 2017.

International Search report for PCT/US2008/052025 dated Sep. 1, 2009.

Partial International Search Report for PCT/US2008/052025, dated Feb. 6, 2009.

* cited by examiner

EXTENDED TIP SPRAY APPLICATOR FOR TWO-COMPONENT SURGICAL SEALANT, AND METHODS OF USE THEREOF

RELATED APPLICATION

This application claims benefit of U.S. Provisional Patent Application No. 61/975,328, filed Apr. 4, 2014.

BACKGROUND OF THE INVENTION

Approximately 1.2 million craniotomy and 6 million spinal procedures are performed annually worldwide. Of those, approximately half of both types of procedures are performed in the United States. Each of these procedures generally requires watertight closure of the dura mater (dura), the leathery membrane that surrounds and protects the brain and spinal cord within their bony confines.

There exists a major unmet need for a product that consistently applies a hydrogel sealant during multiple applications to confined, hard to reach areas of the cranium and spine, creating a watertight dural closure that prevents cerebrospinal fluid (CSF) leakage. Leakage can occur at suture pinholes, incidental tears or other small gaps in the dura. Serious complication can occur including: extra-dural and subcutaneous collections of CSF, known as pseudo-meningoceles, acute and chronic problems of wound healing due to CSF collection, compression of neurological tissues, meningitis, encephalitis, headaches, infection, cognitive changes, additional surgical interventions, prolonged hospitalization, and increased cost. Conventional techniques of preventing CSF leaks are often insufficient because they may not completely stop CSF leaks.

Applicant has developed and markets a two-component hydrogel dural sealant suitable for use as an adjunct to standard methods of dural repair, such as sutures, to provide watertight closure to incised or otherwise compromised dura and as an adhesion barrier to limit post-surgical peridural fibrosis and adhesions. U.S. Pat. No. 8,410,189; U.S. Patent Application Publication No. 2007/0196454; both of which are incorporated herein by reference. The two components are a polyalkyleneimine, such as polyethyleneimine (PEI), and a crosslinking reagent which causes the polyalkyleneimine polymers to polymerize, thereby forming a seal. In certain instances, the crosslinking reagent is a polyethylene glycol (PEG) having reactive terminal groups. Generally, the polyalkyleneimine and crosslinking reagent components are combined shortly before or during their application so that they crosslink in situ in the desired location.

Applicant has also developed and markets a number of applicators suitable for use with the two-component dural sealant. U.S. Pat. Nos. 8,323,262; 8,343,183; 8,262,608; U.S. Patent Application Publication No. 2010/0280547; U.S. Patent Application Publication No. 2013/0338631; all of which are incorporated herein by reference.

SUMMARY OF THE INVENTION

An aspect of the invention is a tip assembly, comprising
a proximal end, comprising a Y fitting, the Y fitting comprising
a first proximal end (1);
a second proximal end (2);
a distal end (3);
a first fluid channel (4) extending from the first proximal end to the distal end; and
a second fluid channel (5) extending from the second proximal end to the distal end;
a distal end;
a mixing nozzle (12), comprising
a proximal end (8), comprising a fluid inlet;
a distal end (9), comprising a fluid outlet (13), wherein the distal end of the mixing nozzle corresponds to the distal end of the tip assembly; and
a mixing chamber (10) disposed between and in fluid communication with the fluid inlet and the fluid outlet;
a tube extending from the distal end of the Y fitting to the proximal end of the mixing nozzle;
a first cannula (6), disposed within and extending along substantially the entire length of the tube, in fluid communication with the first fluid channel of the Y fitting and the fluid inlet of the mixing nozzle; and
a second cannula (7), disposed within and extending along substantially the entire length of the tube, in fluid communication with the second fluid channel of the Y fitting and the fluid inlet of the mixing nozzle;
wherein the tube, the first cannula, and the second cannula are flexible.

An aspect of the invention is a multi-component delivery system, comprising the tip assembly described herein. In a preferred embodiment, the tip assembly of the invention is substituted for the corresponding tip assembly in the multi-component delivery system disclosed in U.S. Patent Application Publication No. 2013/0338631, the entire content of which is incorporated herein by reference.

An aspect of the invention is a method of using the tip assembly of the invention. The method comprises the steps of:
bringing a source of a first component of a two-component hydrogel into fluid communication with the first fluid channel;
bringing a source of a second component of a two-component hydrogel into fluid communication with the second fluid channel;
causing the first component to traverse the first cannula;
causing the second component to traverse the second cannula;
causing the first component to mix with the second component within the mixing chamber, thereby forming a pre-hydrogel mixture; and
expelling the pre-hydrogel mixture through the fluid outlet of the mixing nozzle, thereby forming a spray of the pre-hydrogel mixture.

DETAILED DESCRIPTION OF THE INVENTION

Neurosurgical procedures, such as craniotomy and spinal surgery, frequently involve penetration of the dura mater. Many of these procedures are characterized by sites with limited or difficult access owing to their anatomy and/or the use of minimally invasive techniques and equipment. For example, certain infratentorial, skull base, and spinal surgical procedures present limited or difficult access.

Applicant currently markets, as Adherus AutoSpray Dural Sealant, a sterile, single-use, electromechanical, battery-operated device with internal system components that (i) provide air flow to aid in the delivery of a synthetic, absorbable, two-component hydrogel sealant system, and (ii) allow delivery to be interrupted without clogging. The device is supplied as a pre-assembled applicator and two separate glass vials containing the crosslinking components which, when prepared and mixed, create hyperbranched globular structures through the crosslinking of a polyfunctional nucleophile with a bifunctional electrophile. The product is simple to prepare and, once applied to the dural surface, quickly cures to form a watertight seal. Adherus AutoSpray Dural Sealant is a single-use device supplied terminally sterilized by radiation. See U.S. Patent Application Publication No. 2013/0338631, the entire content of which is incorporated herein by reference.

Figure 1:
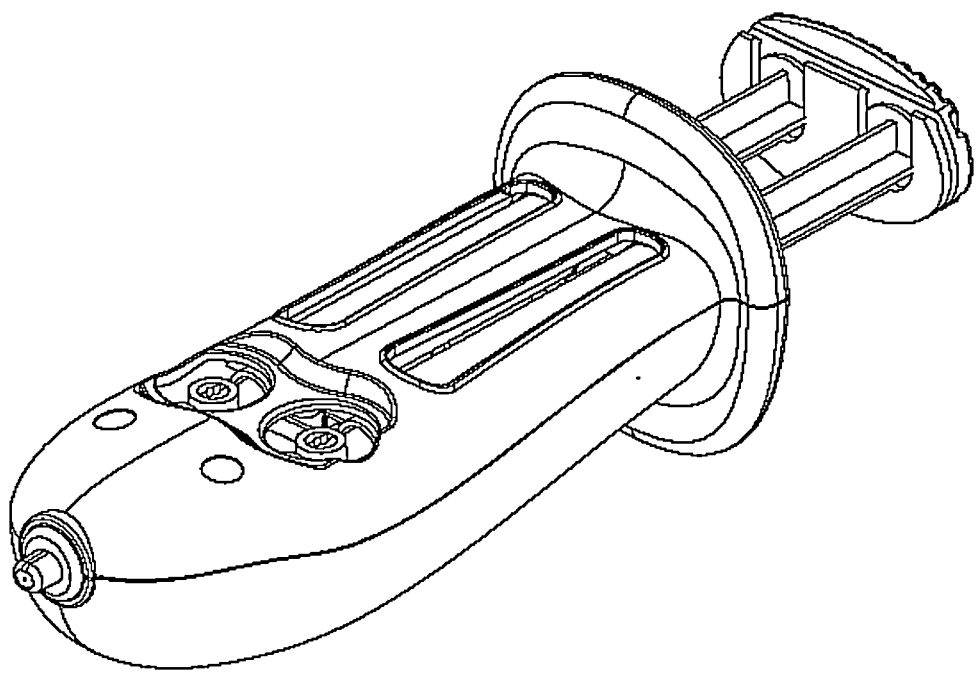
FIG. 1 depicts an applicator with a short tip shown at the left.
Figure 1:
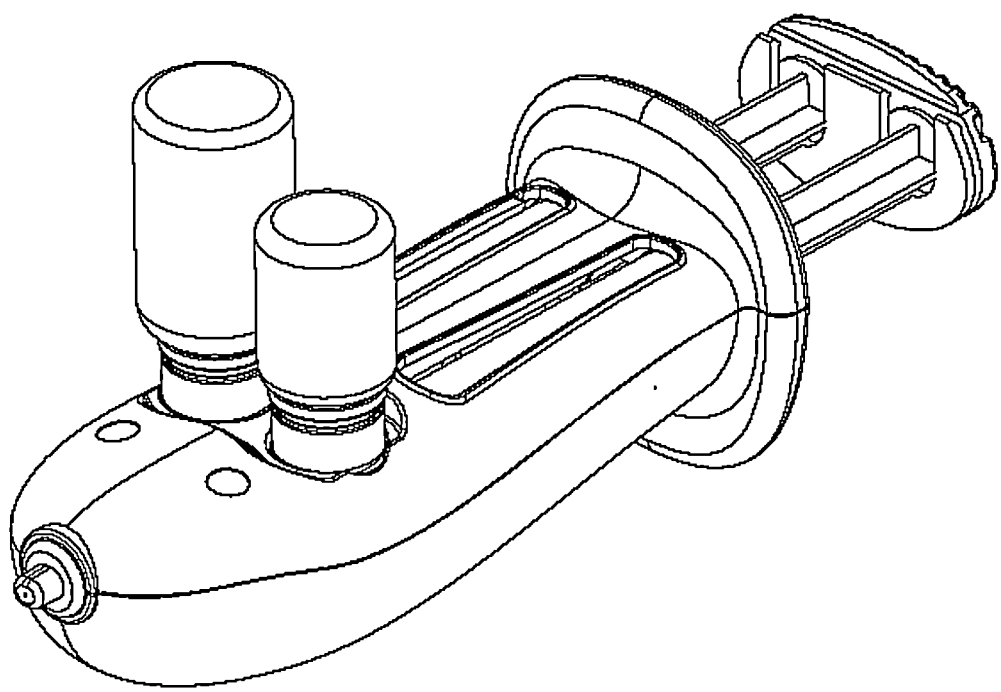

The Adherus AutoSpray Dural Sealant has a relatively short or "stub-nosed" or "snub-nosed" tip which creates a locally directed spray comprised of the combined components of the hydrogel sealant. See FIG. 1. The standard length tip is well suited for use in procedures with relatively wide surgical access.

The instant invention provides an extended and flexible tip suitable for use in delivering a two-component liquid composition as a locally directed spray. The extended, flexible tip is specifically useful in conjunction with delivery of a two-component hydrogel sealant, such as is described in U.S. Pat. No. 8,410,189 and U.S. Patent Application Publication No. 2007/0196454 (both of which are incorporated by reference). Additionally, the extended, flexible tip is specifically useful as a modification of the Adherus AutoSpray Dural Sealant described above, whereby the extended, flexible tip of the invention is substituted for the snub-nosed, standard length tip of the applicator device/system.

Advantages of the extended, flexible tip of the invention include its ability to access confined, hard-to-reach surgical sites that otherwise allow only limited access, such as infratentorial, skull base (e.g., transsphenoidal), and spinal sites; and the ability to provide improved visualization for the operator during use. For example, the extended length of the tip permits improved accessibility, and the flexibility of the tip permits positioning of the applicator handset out of the line of sight of the applicator tip.

In one embodiment, the extended, flexible tip of the invention is incorporated into a pre-assembled, ready-for-use sterile applicator that reduces preparation time and allows the controlled application of a hydrogel formulation within confined, hard-to-reach areas, e.g., of the cranium and spine, without clogging. For example, the extended, flexible tip may be incorporated into a sterile, single-use, electromechanical, battery operated, device with internal system components that provide air flow to aid in the delivery of a synthetic, absorbable, two-component hydrogel sealant system and allow delivery to be interrupted without clogging. In one embodiment the device is supplied as a pre-assembled applicator and two separate glass vials containing the crosslinking components which, when prepared and mixed, create hyperbranched globular structures through the crosslinking of a polyfunctional nucleophile with a bifunctional electrophile.

An aspect of the invention is a tip assembly, comprising
a proximal end, comprising a Y fitting, the Y fitting comprising
    a first proximal end;
    a second proximal end;
    a distal end;
    a first fluid channel extending from the first proximal end to the distal end; and
    a second fluid channel extending from the second proximal end to the distal end;
a distal end;
a mixing nozzle, comprising
    a proximal end, comprising a fluid inlet;
    a distal end, comprising a fluid outlet, wherein the distal end of the mixing nozzle corresponds to the distal end of the tip assembly; and
    a mixing chamber disposed between and in fluid communication with the fluid inlet and the fluid outlet;
a tube extending from the distal end of the Y fitting to the proximal end of the mixing nozzle;
a first cannula, disposed within and extending along substantially the entire length of the tube, in fluid communication with the first fluid channel of the Y fitting and the fluid inlet of the mixing nozzle; and
a second cannula, disposed within and extending along substantially the entire length of the tube, in fluid communication with the second fluid channel of the Y fitting and the fluid inlet of the mixing nozzle;
wherein the tube, the first cannula, and the second cannula are flexible.

In an embodiment, the first cannula further extends along substantially the entire length of the first fluid channel of the Y fitting; and the second cannula further extends along substantially the entire length of the second fluid channel of the Y fitting. In such an embodiment the Y fitting can be formed, for example, by injection molding around at least a portion of the proximal ends of the cannulae.

In certain embodiments, the first cannula and the second cannula are made of annealed stainless steel tubing. The annealed stainless steel tubing provides a desirable combination of both stiffness and flexibility, e.g., bendability.

In certain embodiments, the cannulae are identical in length and inside diameter.

In certain embodiments, the cannulae have an inside diameter of about 0.03 inches (0.76 millimeters (mm)) to about 0.05 inches (1.27 mm).

In certain embodiments, the length of the assembly from the distal end of the Y fitting to the distal end of the mixing nozzle is about 12 centimeters (cm) to about 20 cm.

In certain embodiments, the length of the assembly from the distal end of the Y fitting to the distal end of the mixing nozzle is about 12 cm to about 15 cm.

In certain embodiments, the length of the assembly from the distal end of the Y fitting to the distal end of the mixing nozzle is about 12 cm.

In certain embodiments, the length of the assembly from the distal end of the Y fitting to the distal end of the mixing nozzle is about 1 cm to less than about 12 cm.

In certain embodiments, the length of the assembly from the distal end of the Y fitting to the distal end of the mixing nozzle is about 1 cm to about 10 cm.

In certain embodiments, the length of the assembly from the distal end of the Y fitting to the distal end of the mixing nozzle is about 1 cm to about 8 cm.

In certain embodiments, the length of the assembly from the distal end of the Y fitting to the distal end of the mixing nozzle is about 1 cm to about 6 cm.

In certain embodiments, the length of the assembly from the distal end of the Y fitting to the distal end of the mixing nozzle is about 1 cm to about 4 cm.

In certain embodiments, the length of the assembly from the distal end of the Y fitting to the distal end of the mixing nozzle is about 2 cm to less than about 12 cm.

In certain embodiments, the length of the assembly from the distal end of the Y fitting to the distal end of the mixing nozzle is about 2 cm to about 10 cm.

In certain embodiments, the length of the assembly from the distal end of the Y fitting to the distal end of the mixing nozzle is about 2 cm to about 8 cm.

In certain embodiments, the length of the assembly from the distal end of the Y fitting to the distal end of the mixing nozzle is about 2 cm to about 6 cm.

In certain embodiments, the length of the assembly from the distal end of the Y fitting to the distal end of the mixing nozzle is about 2 cm to about 4 cm.

Figure 2:
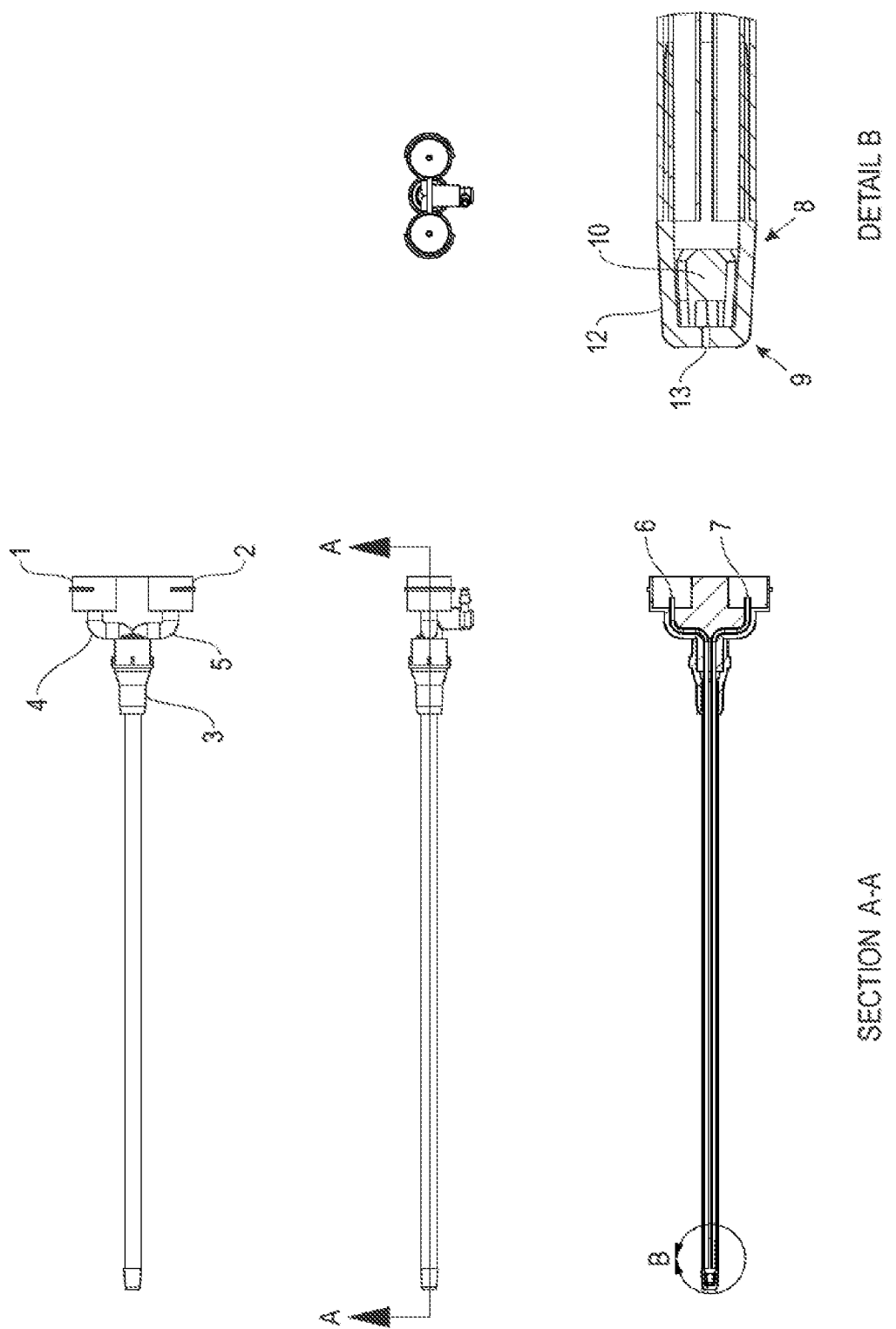
FIG. 2 depicts top, side, end-on, section, and detail section views of a tip of the invention.
Figure 3:
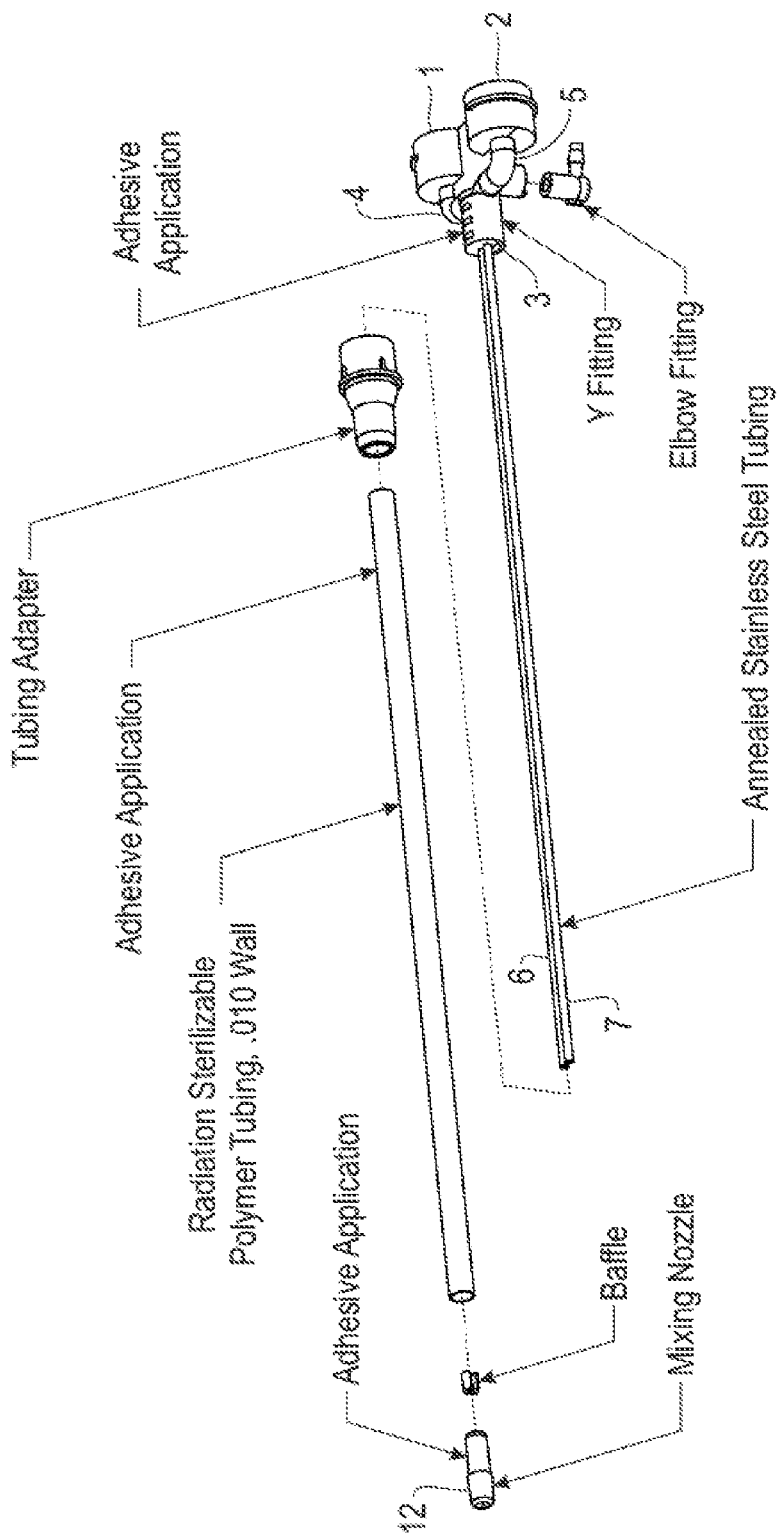
FIG. 3 depicts an exploded view of the tip of FIG. 2.

In certain embodiments, the tip assembly further comprises a tubing adapter which, as a sleeve, accepts the distal end of the Y fitting and the proximal end of the tube. See FIG. 2 and FIG. 3.

In certain embodiments, the length of the assembly from the distal end of the tubing adapter to the distal end of the mixing nozzle is about 12 centimeters (cm) to about 20 cm.

In certain embodiments, the length of the assembly from the distal end of the tubing adapter to the distal end of the mixing nozzle is about 12 cm to about 15 cm.

In certain embodiments, the length of the assembly from the distal end of the tubing adapter to the distal end of the mixing nozzle is about 12 cm.

In certain embodiments, the length of the assembly from the distal end of the tubing adapter to the distal end of the mixing nozzle is about 1 cm to less than about 12 cm.

In certain embodiments, the length of the assembly from the distal end of the tubing adapter to the distal end of the mixing nozzle is about 1 cm to about 10 cm.

In certain embodiments, the length of the assembly from the distal end of the tubing adapter to the distal end of the mixing nozzle is about 1 cm to about 8 cm.

In certain embodiments, the length of the assembly from the distal end of the tubing adapter to the distal end of the mixing nozzle is about 1 cm to about 6 cm.

In certain embodiments, the length of the assembly from the distal end of the tubing adapter to the distal end of the mixing nozzle is about 1 cm to about 4 cm.

In certain embodiments, the length of the assembly from the distal end of the tubing adapter to the distal end of the mixing nozzle is about 2 cm to less than about 12 cm.

In certain embodiments, the length of the assembly from the distal end of the tubing adapter to the distal end of the mixing nozzle is about 2 cm to about 10 cm.

In certain embodiments, the length of the assembly from the distal end of the tubing adapter to the distal end of the mixing nozzle is about 2 cm to about 8 cm.

In certain embodiments, the length of the assembly from the distal end of the tubing adapter to the distal end of the mixing nozzle is about 2 cm to about 6 cm.

In certain embodiments, the length of the assembly from the distal end of the tubing adapter to the distal end of the mixing nozzle is about 2 cm to about 4 cm.

In certain embodiments, the tip assembly further comprises a third fluid channel, wherein the third fluid channel is defined by and extends from a proximal inlet of the Y fitting, along and within the tube, to a distal outlet in fluid communication with the mixing chamber of the mixing nozzle.

In certain embodiments, the proximal inlet of the Y fitting comprises a fitting suitable for receiving a gas from a gas reservoir or source of gas. In one embodiment, the gas is air. The gas reservoir or source of gas may be a gas-pump that is a built-in component of an applicator.

In certain embodiments, the tube comprises polymeric material that may be sterilized by radiation.

In certain embodiments, the tube is made of polytetrafluoroethylene (Teflon®, DuPont).

In certain embodiments, the tube is made from phthalate-free medical grade polyvinyl chloride (PVC).

In certain embodiments, the tube has a maximum outside diameter of about 5.5 millimeters (mm), and the mixing nozzle has a maximum outside diameter of about 5.5 mm.

In certain embodiments, the tube has a maximum outside diameter of about 5.2 mm, and the mixing nozzle has a maximum outside diameter of about 5.2 mm.

In certain embodiments, the tube and its contents together can be bent at least 30° over a 2.25-inch span upon application of force no less than about 1 pound and no more than about 24 pounds. Advantageously, the tube and its contents (e.g., the two cannulae) can be readily bent by hand, with or without the aid of any tool, thereby permitting operating room personnel (e.g., surgeon) the ability to conform, and even re-conform, the tube to a shape of choice.

Figure 4:
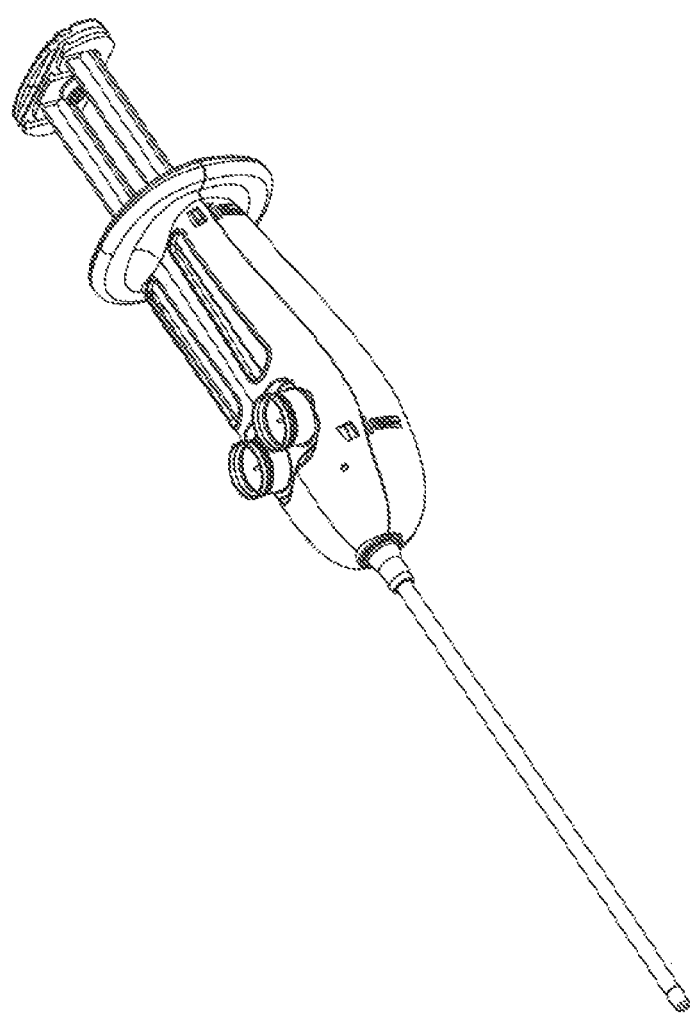
FIG. 4 depicts an exterior view of a tip of the invention assembled together with an applicator.
Figure 5:
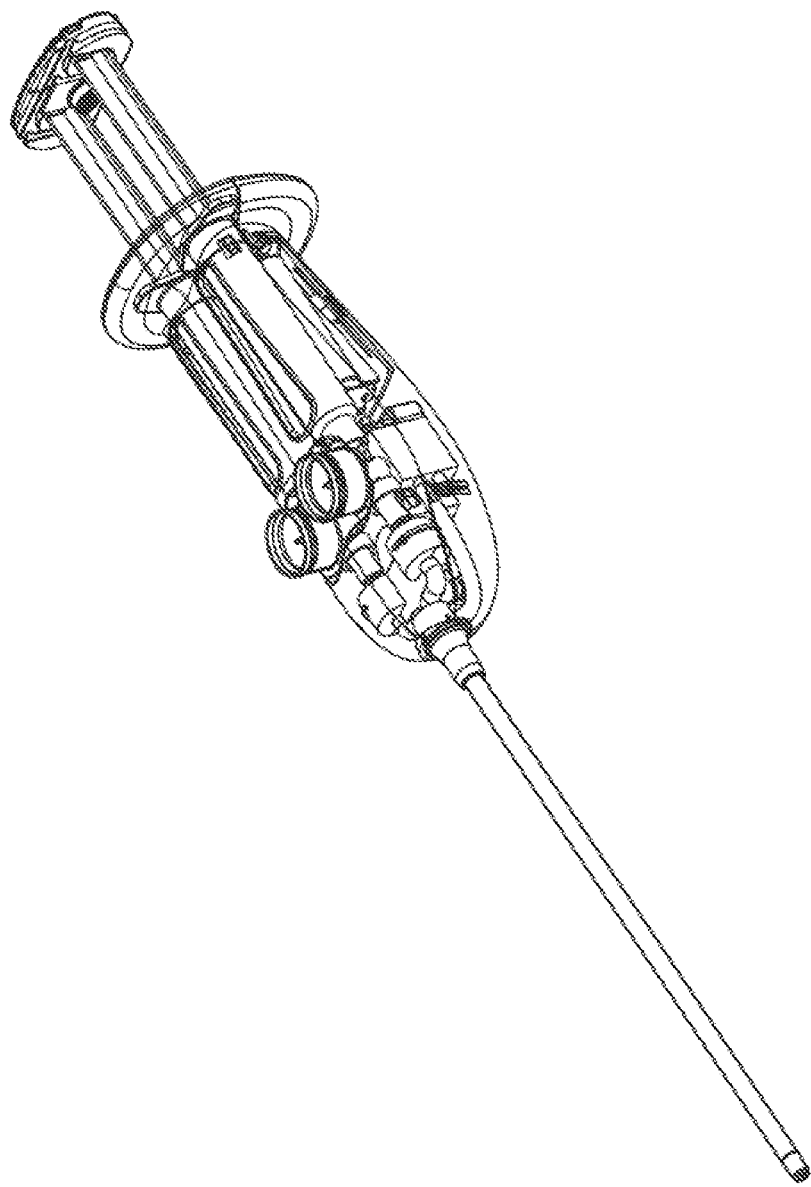
FIG. 5 depicts a transparent view of a tip of the invention assembled in combination with an applicator as in FIG. 4.

An aspect of the invention is a multi-component delivery system, comprising the tip assembly described herein. In a preferred embodiment, the tip assembly of the invention is substituted for the corresponding tip assembly in the multi-component delivery system disclosed in U.S. Patent Application Publication No. 2013/0338631, the entire content of which is incorporated herein by reference. See FIG. 4 and FIG. 5. In one embodiment, the Y fitting is enclosed within the handset of the system, while substantially the remainder of the tip assembly—including the tube and its contents, at least a distal portion of the tubing adapter (if present), and the mixing nozzle—projects and extends distally from the housing of the handset. See FIG. 4 and FIG. 5.

An aspect of the invention is a method of using the tip assembly of the invention. The method comprises the steps of:
bringing a source of a first component of a two-component system into fluid communication with the first fluid channel;
bringing a source of a second component of a two-component system into fluid communication with the second fluid channel;
causing the first component to traverse the first cannula;
causing the second component to traverse the second cannula;
causing the first component to mix with the second component within the mixing chamber, thereby forming a mixture; and
expelling the mixture through the fluid outlet of the mixing nozzle, thereby forming a spray of the mixture.

In an embodiment, the first component and the second component are components of an adhesive. For example, the first component and the second component can be a urethane and a fibrin, respectively. As another example, the first component and the second component can be a polyalkyleneimine and an activated PEG, respectively. As yet another example, the first component and the second component can be PEI and an activated PEG, respectively.

In an embodiment, the first component and the second component are components of a sealant. For example, the first component and the second component can be a urethane and a fibrin, respectively. As another example, the first component and the second component can be a polyalkyleneimine and an activated PEG, respectively. As yet another example, the first component and the second component can be PEI and an activated PEG, respectively.

In an embodiment, at least one of the first component and the second component can comprise a drug or other biologically active component.

In an embodiment, at least one of the first component and the second component is a drug or other biologically active component.

In an embodiment, the method further comprises bending the tube and its contents. For example, the tube and its contents may be bent an amount sufficient to permit improved access to a surgical site having limited or difficult access. In certain embodiments, the tube and its contents may be bent an amount sufficient to permit improved line of sight for the operator (e.g., surgeon).

In certain embodiments, the tube and its contents can be bent in one or more locations. In certain embodiments, the tube and its contents can be bent in one location. In certain embodiments, the tube and its contents can be bent in two locations. In certain embodiments, the tube and its contents can be bent in three locations. When there is more than one bend, each bend can be made independent of any other, in terms of acuity, direction, and plane.

In respect of each bend, in certain embodiments, the tube and its contents may be bent by up to about 10°. In respect of each bend, in certain embodiments, the tube and its contents may be bent by up to about 20°. In respect of each bend, in certain embodiments, the tube and its contents may be bent by up to about 30°. In respect of each bend, in certain embodiments, the tube and its contents may be bent by up to about 40°. In respect of each bend, in certain embodiments, the tube and its contents may be bent by up to about 45°.

An aspect of the invention is a method of using the tip assembly of the invention. The method comprises the steps of:
  bringing a source of a first component of a two-component hydrogel into fluid communication with the first fluid channel;
  bringing a source of a second component of a two-component hydrogel into fluid communication with the second fluid channel;
  causing the first component to traverse the first cannula;
  causing the second component to traverse the second cannula;
  causing the first component to mix with the second component within the mixing chamber, thereby forming a pre-hydrogel mixture; and
  expelling the pre-hydrogel mixture through the fluid outlet of the mixing nozzle, thereby forming a spray of the pre-hydrogel mixture.

In an embodiment, the method further comprises bending the tube and its contents. For example, the tube and its contents may be bent an amount sufficient to permit improved access to a surgical site having limited or difficult access. In certain embodiments, the tube and its contents may be bent an amount sufficient to permit improved line of sight for the operator (e.g., surgeon).

In certain embodiments, the tube and its contents can be bent in one or more locations. In certain embodiments, the tube and its contents can be bent in one location. In certain embodiments, the tube and its contents can be bent in two locations. In certain embodiments, the tube and its contents can be bent in three locations. When there is more than one bend, each bend can be made independent of any other, in terms of acuity, direction, and plane.

In respect of each bend, in certain embodiments, the tube and its contents may be bent by up to about 10°. In respect of each bend, in certain embodiments, the tube and its contents may be bent by up to about 20°. In respect of each bend, in certain embodiments, the tube and its contents may be bent by up to about 30°. In respect of each bend, in certain embodiments, the tube and its contents may be bent by up to about 40°. In respect of each bend, in certain embodiments, the tube and its contents may be bent by up to about 45°.

In an embodiment, the spray is applied to dura mater of a subject.

In an embodiment, the dura mater is cranial dura mater.

In an embodiment, the dura mater is spinal dura mater.

In certain embodiments, the method is part of a neurosurgical procedure.

In an embodiment, the neurosurgical procedure is infratentorial craniotomy.

In an embodiment, the neurosurgical procedure is skull base craniotomy.

In an embodiment, the neurosurgical procedure is transsphenoidal craniotomy.

In an embodiment, the neurosurgical procedure is surgery on the spine.

In certain embodiments, the spray is applied to a mesh implant, e.g., a hernia repair mesh, in situ.

In certain embodiments, the spray is applied to a tissue of interest to prevent or reduce the development of adhesion formation between the tissue of interest and another tissue.

In certain embodiments, the method is part of a hernia repair procedure, e.g., a femoral, inguinal, or abdominal hernia repair.

In certain embodiments, the method is part of an abdominal surgical procedure, including, without limitation, exploratory laparotomy, stomach or bowel resection or repair, bowel reanastomosis, gastroplasty, appendectomy, cholecystectomy, splenectomy, nephrectomy, tubal ligation or resection, tumor resection, and repair of abdominal aortic aneurysm.

In certain embodiments, the method is part of a thoracic surgical procedure.

The invention further contemplates methods of using the tip assembly of the invention with only a single component. For example, also contemplated is a method comprising the steps of:

- bringing a source of a component into fluid communication with the first fluid channel;
- causing the component to traverse the first cannula; and
- expelling the component through the fluid outlet of the mixing nozzle, thereby forming a spray of the component.

The invention now being generally described, it will be more readily understood by reference to the following examples, which are included merely for purposes of illustration of certain aspects and embodiments of the present invention, and are not intended to limit the invention.

EXAMPLES

Example 1

All tubing (cannulae) was 1/16" outside diameter, annealed stainless steel. Teflon tubing was used as the exterior polymer tubing sheath (tube).

Results a) Samples with 0.030" inside diameter (ID) tubing had very little dripping during start-and-stop operations. Gravimetric swelling=22.4±6.22 (mean±std. dev) percent vs. 18% on control units of same formulation but current stub-nose AutoSpray.
b) Samples with 0.020" inside diameter exhibited much worse spray behavior.
Lots of dripping of PEG solution during stop operation (with air pump on).
Gravimetric swelling=24.8±3.1%

Gravimetric swelling is a measure of the completeness of mixing and polymerization. If not well mixed, or if the two liquids are not proportioned correctly, the swelling will be higher.

CONCLUSION: Unexpectedly, the larger inside diameter was better. (Prior to experiment I would have predicted a smaller inside diameter would be better, i.e., have less of a chance to allow PEG or PEI solution to leak out during stop operation.

Example 2

Tubing (cannulae) with 0.030", 0.040" and 0.046" ID.

a) 0.030" ID samples—Same performance as Example 1. Small amount of drips during stop operation. Gravimetric swelling=25.0±4.14% b) 0.040" ID samples—Similar dripping performance as 0.030" samples. Gravimetric swelling=24.3±4.9% c) 0.046" ID samples—Noticeably improved drip performance over 0.030" and 0.040" samples. Gravimetric swelling=14.3±3.05%

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A tip assembly, comprising a proximal end, comprising a Y fitting, the Y fitting comprising a first proximal end;

a second proximal end, the first and second proximal ends connected to an applicator;

a distal end;

a first fluid channel extending from the first proximal end to the distal end, the first fluid channel including a first section and a second section perpendicular to the first section; and a second fluid channel extending from the second proximal end to the distal end, the second fluid channel including a third section and a fourth section perpendicular to the third section;

a distal end;

a mixing nozzle, comprising a proximal end, comprising a fluid inlet;

a distal end, comprising a fluid outlet, wherein the distal end of the mixing nozzle corresponds to the distal end of the tip assembly; and a mixing chamber disposed between and in fluid communication with the fluid inlet and the fluid outlet;

a tube extending from the distal end of the Y fitting to the proximal end of the mixing nozzle, the tube defining a tube cross section;

a first cannula, disposed within and extending along substantially the entire length of the tube, in fluid communication with the first fluid channel of the Y fitting and the fluid inlet of the mixing nozzle, the first cannula being perpendicular to the second section of the first channel, the first cannula defining a first cross section;

a second cannula, disposed within and extending along substantially the entire length of the tube, in fluid communication with the second fluid channel of the Y fitting and the fluid inlet of the mixing nozzle, the second cannula being perpendicular to the fourth section of the second channel, the second cannula defining a second cross section, and a third fluid channel extending from a proximal inlet of the Y fitting to a distal outlet in fluid communication with the mixing chamber of the mixing nozzle, the third fluid channel having a third cross section, wherein the third cross section is equal to the tube cross section minus the first and second cross sections, the third fluid channel being in fluid communication with a built-in gas pump of the applicator, wherein the tube, the first cannula, and the second cannula are flexible.

2. The tip assembly of claim 1, wherein the first cannula further extends along substantially the entire length of the first fluid channel of the Y fitting; and the second cannula further extends along substantially the entire length of the second fluid channel of the Y fitting.

3. The tip assembly of claim 1, wherein the length of the assembly from the distal end of the Y fitting to the distal end of the mixing nozzle is about 12 cm to about 20 cm.

4. The tip assembly of claim 3, wherein the length of the assembly from the distal end of the Y fitting to the distal end of the mixing nozzle is about 12 cm to about 15 cm.

5. The tip assembly of claim 3, wherein the length of the assembly from the distal end of the Y fitting to the distal end of the mixing nozzle is about 12 cm.

6. The tip assembly of claim 1, wherein the tube comprises polymeric material that may be sterilized by radiation.

7. The tip assembly of claim 6, wherein the tube is made of polytetrafluoroethylene.

8. The tip assembly of claim 6, wherein the tube is made from phthalate-free medical grade polyvinyl chloride (PVC).

9. The tip assembly of claim 1, wherein the tube has a maximum outside diameter of about 5.5 millimeters (mm), and the mixing nozzle has a maximum outside diameter of about 5.5 mm.

10. The tip assembly of claim 9, wherein the tube has a maximum outside diameter of about 5.2 mm, and the mixing nozzle has a maximum outside diameter of about 5.2 mm.

11. A multi-component delivery system, comprising the tip assembly of claim 1.

12. The tip assembly of claim 1, wherein the first cannula and the second cannula have an inside diameter of about 0.03 inches.

13. The tip assembly of claim 1, wherein the first cannula and the second cannula have an inside diameter of about 0.046 inches.

14. A method of using the tip assembly of claim 1, comprising bringing a source of a first component of a two-component hydrogel into fluid communication with the first fluid channel;

bringing a source of a second component of a two-component hydrogel into fluid communication with the second fluid channel;

causing the first component to traverse the first cannula;

causing the second component to traverse the second cannula;

causing the first component to mix with the second component within the mixing chamber, thereby forming a pre-hydrogel mixture; and expelling the pre-hydrogel mixture through the fluid outlet of the mixing nozzle, thereby forming a spray of the pre-hydrogel mixture.

15. The method of claim 14, further comprising bending the tube and its contents.

16. The method of claim 14, wherein said spray is applied to dura mater of a subject.

17. The method of claim 16, wherein said dura mater is cranial dura mater.

18. The method of claim 16, wherein said dura mater is spinal dura mater.

19. The method of claim 14, wherein the method is part of a neurosurgical procedure.

20. The method of claim 19, wherein the neurosurgical procedure is infratentorial craniotomy.

21. The method of claim 19, wherein the neurosurgical procedure is skull base craniotomy.

22. The method of claim 19, wherein the neurosurgical procedure is transsphenoidal craniotomy.

23. The method of claim 19, wherein the neurosurgical procedure is surgery on the spine.

* * * * *